(12) United States Patent
Zun

(10) Patent No.: US 6,755,646 B2
(45) Date of Patent: Jun. 29, 2004

(54) TOOTH COLOR APPROXIMATING SYSTEM

(76) Inventor: Samuel K. Zun, 640 Evening Star La., Cincinnati, OH (US) 45220

( * ) Notice: Subject to any disclaimer, the term of this patent is extended or adjusted under 35 U.S.C. 154(b) by 108 days.

(21) Appl. No.: 10/034,868

(22) Filed: Dec. 27, 2001

(65) Prior Publication Data

US 2003/0124481 A1 Jul. 3, 2003

(51) Int. Cl.$^7$ ............................................... A61C 19/10
(52) U.S. Cl. ........................................................ 433/26
(58) Field of Search .......................................... 433/26

(56) References Cited

U.S. PATENT DOCUMENTS

| | | | |
|---|---|---|---|
| 3,964,167 A | | 6/1976 | Yerkes ......................... 433/26 |
| 4,608,015 A | * | 8/1986 | Smigel ......................... 433/26 |
| 4,978,296 A | | 12/1990 | Antons et al. ................. 433/26 |
| 5,004,417 A | | 4/1991 | Giaramita ..................... 433/26 |
| 5,240,414 A | * | 8/1993 | Thompson .................... 433/26 |
| 5,588,834 A | | 12/1996 | Resk et al. .................... 433/26 |
| 5,639,235 A | * | 6/1997 | Lapointe et al. .............. 433/26 |
| 5,653,589 A | | 8/1997 | Kleinmann ................... 433/26 |
| 5,743,730 A | | 4/1998 | Clester et al. ................. 433/26 |
| 5,961,324 A | | 10/1999 | Lehmann ...................... 433/26 |
| 6,132,210 A | | 10/2000 | Lehmann ...................... 433/26 |
| 6,305,933 B1 | | 10/2001 | Lehmann ...................... 433/26 |

OTHER PUBLICATIONS

Rich Cook, *A Guide to Understanding Color Communication*, X-Rite, Incorporated, 2000, 1–28.

Ernst A. Hegenbarth, *Creative Ceramic Color: A Practical System*, Quintessence Books, Quintessence Publishing Co., Chicago, 1989, 2 pages.

Paul J. Muia, *The Four Dimensional Tooth Color System*, Quintessence Books, Quintessence Publishing Co., Chicago, 1985, pp. 44–49.

Vanini and Mangani, *Determination and Communication of Color Using the Five Color Dimensions of Teeth*, Practical Procedures and Aesthetic Dentistry, 2001, vol. 13, No. 1, pp. 19–26.

* cited by examiner

Primary Examiner—John J. Wilson
(74) Attorney, Agent, or Firm—Wood, Herron & Evans, L.L.P.

(57) ABSTRACT

A dental color matching system. A series of translucent films are printed with a variety of colors that closely approximate the colors found in human teeth. The films, or sections of the films, may be reversibly self-adhesive for ease in placing on and removing from a template, or on top of one another, in a sequence until the desired or matching color is obtained. The color is communicated among dental professionals and patient, for example, by indicia that encode the different colors found in a shade system used by dental professionals or in the tooth itself. By using the invention, a dental professional can thus economically and efficiently prepare a dental prosthesis with a color that closely matches that of a patient's natural tooth.

9 Claims, 1 Drawing Sheet

TOOTH COLOR APPROXIMATING SYSTEM

FIELD OF THE INVENTION

The invention relates to a method and apparatus to improve approximation of the color of teeth and communication of this color.

BACKGROUND OF THE INVENTION

The recent development of dental porcelain allows a skilled dental technician to produce a dental prosthesis that closely approximates the natural state, if provided with accurate information of the color of a tooth (or teeth) to be restored. To produce a lifelike dental prosthesis, such as a crown, bridge, etc., dental professionals must communicate among themselves and to patients the often subtle differences in color that are found in human teeth. When formulating the prosthesis, it is important that dentists, dental technicians, and patients refer to the same color.

One of the most commonly used devices to match tooth color has been the dental shade guide. The shade guide, usually made of porcelain or plastic, is commercially available under names such as Vita-Lumin™ (Vita), Bioform™ (Dentsply), and Vitapan 3-D Master™ (Vita).

Such commercial color guides, however, have limited use for several reasons. One reason is that the colors in the guides are not able to match the subtle differences of the colors found in human teeth. Another reason is that the shade guides are grouped in terms of chroma, hue, and value on the basis of the Munsell Chromatic Scale. A dental professional is forced to describe tooth color, which is not a logical system, by a logical system consisting of a letter, a number, or both together. A third reason is that the porcelains or plastics used to make the shade guides are of different quality from the porcelains used by dental professionals in fabricating the prosthesis. The resulting product is frequently of a different color than that of the natural tooth of a patient. Even if the color is closely matched, the subtle differences of individual tooth/teeth color(s) resulting from different values are often ignored or compromised. This diminishes the aesthetic appearance of the prosthesis.

To overcome the problems which accompany the use of commercial shade guides, there have been attempts by dental professionals to produce custom-made shade guides for their own use. Several colored samples of plastic, porcelain, or other materials are usually made to match the various colors of different parts of an individual tooth. This method, however, is very expensive, time-consuming, and the results are not always satisfactory. To remedy the situation, extrinsic modifications of commercial dental color guides also have been attempted. For example, gray plastic or porcelain facets have been made which adapt to an individual shade tab of a shade or color guide to match the value of a tooth, that is, its translucent grayness. This is described by Ubassy in *Shape and Color, The Key to Successful Ceramic Restoration*, Quintessence Publishing Co., Inc., Chicago (1995). However, more than the difference of value describes the subtlety of colors of human teeth. In addition, the majority of dentists cannot afford to fabricate individual plastic facets or porcelain chips or tabs each time they are needed. There have also been attempts to modify the shade guides by "staining" them. While this may be of some benefit in matching color, it cannot include value.

Other methods to describe the range of colors in human teeth use photographs, slides, or drawings with accompanying description of colors and, in recent years, computer images via the Internet. These methods are limited because the images are influenced by many different factors such as the quality of films, monitors, or cameras. For example, the same image of a tooth viewed on one type of monitor may be different from that when viewed on a different monitor.

Photometers, spectrophotometers, and various digitized and computerized devices have also been introduced to analyze and communicate the color of teeth. Many of these devices are not perfected as yet, and are not practical for the majority of dental professionals because of their cost and/or complexity. Furthermore, even when using these electronic devices, the analyses are still described and communicated in letters, numbers, or both, rather than in color.

There is thus a need for a method to communicate color that is economical, accurate, amenable to use for more than one patient, and easy to use in a dental office.

SUMMARY OF THE INVENTION

The invention is directed to a system, and a method of using the system, of a plurality of translucent films having color distributions and/or shades of color found in human teeth, which are used to convey these color distributions among dental professionals and patients. It is understood for this invention that color encompasses both color and the various shades of a particular color. The films may be reversibly self-adhesive for placement or alignment on a template, or on top of another film, until the desired or matching color is achieved. The color to be matched may be that of the entire tooth, or only a section of the tooth. This sequence of films, providing the desired color for each area of the tooth, is conveyed among dental professionals and patients by indicia for the colors. In this way, the system allows the precise, or closely approximated, colors for the areas to be communicated. Subsequently, a dental prosthesis can be made having colors that closely approximate all areas of a patient's natural tooth, relative to either the tooth or to commercial shade guides.

In one embodiment, the system contains a series of these translucent films in a plurality of the colors found in human teeth. In another embodiment, the colors match those of dental porcelain powders that are used in preparing dental prostheses. The films may be in a variety of sizes and shapes, and may also have divisions corresponding to different parts or areas of the tooth.

The invention will be further appreciated in light of the following drawings and detailed description.

DETAILED DESCRIPTION

Figure 1:
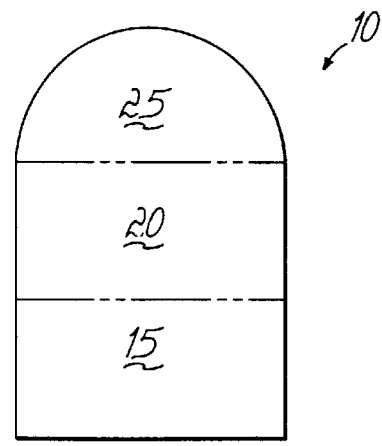
FIG. 1 illustrates three divisions of a tooth.

A system is disclosed for closely approximating the colors, and/or shades of colors, of a dental prosthesis to that of a natural tooth, and communicating these colors to dental professionals using a series of colored, translucent films so that the color of the prosthesis more closely approximates that of the natural tooth. The use of color encompasses the description of color and color shades that is known to one skilled in the art. This includes, and is not limited to, descriptive terms such as chroma, hue, and value. In one embodiment, the films are removably self-adhering. In another embodiment, the films are removably partially self-adhering. In yet another embodiment, the films are non-selfadhering. The films comprise a system, indicating the numerous colors and shades of color found in a tooth and used in different dental porcelain systems to approximate colors in part of a tooth or in the entire tooth. Any dental prosthesis, such as a crown, a bridge, a denture, a partial denture, etc., may be made using information provided by the inventive system. Thus, the system may be used as a color guide or a shade guide by itself.

In producing the films, custom porcelain shade guides are prepared from porcelain powders in a range of colors found in teeth. In recent years, dental porcelain makers have produced powders of a number of different colors which are commonly found in human teeth. For example, the Creative Color System of Degussa porcelain (Degussa-Ney Dental Inc., Bloomfield, Conn.) includes twenty-six different shades, in addition to the regular sixteen dentin colors, four incisal colors, and sixteen opaque colors. The Creation porcelain system produced by Willie Geller (Dental Systems Group, Utica, N.Y.) consists of fifty-nine shades, in addition to the regular sixteen dentin colors, four incisal colors, and sixteen opaque colors.

Porcelain shade guides are a series of tabs or chips, often in the shape of a tooth, and have a thickness of about one-half millimeter. Other types of shade guides may also be used, for example, paper shade guides such as used to show colors of paint. The colors of each of these chips or shade guides are measured, and then inks that match the colors are printed on a series of translucent films. Variations of these colors are also made, for example, using the method of dilution as described by Muia in *The Four Dimensional Tooth Color System* (Quintessence Publishing Co., Inc., Chicago, 1985), the relevant sections of which are expressly incorporated by reference herein in their entirety. This ensures that the inventive shading system encompasses the often subtle differences in color between the porcelain chip, or paper shade guide, and that of a natural tooth.

The colors of the custom or commercially available porcelain shade guides that are prepared from porcelain powders are measured so that a printing ink may be prepared with the precise matching color. Measurement can be done using a spectrophotometer or other type of instrument that expresses colors numerically, as is known to one skilled in the art. For example, a procedure using a spectrophotometer and the associated mathematical calculations for the numerical expression of color is described in *A Guide to Understanding Color Communication* (Monograph L10-001, 1/2000, X-Rite, Incorporated, Grandville, Mich.) which is expressly incorporated by reference herein in its entirety. Briefly, the spectrophotometer measures spectral data, such as the amount of light reflected from an object, at several intervals along the visible spectrum and represents these data as a spectral curve. The data are mathematically transformed into standardized colorimetric terms, which can be used with various color scales for assessment. As recommended by the Commission Internationale de I'Eclairage, two alternate color scales may be used for this assessment. These scales are the CIE 1976 (L*a*b*) or CIELAB scale, and the CIELCH scale (L*C*h°) where L* defines lightness, a* denotes the red/green value, b* denotes the yellow/blue value, C* specifies chroma, and h° denotes hue angle, which is an angular measurement. As described in the monograph, these values are used to calculate a color in a color space using either Cartesian coordinates or polar coordinates in order to accurately define the color.

Using the color assessment derived from these scales, colored printing inks are prepared having the same color assessment as the porcelain chips or shade guides. An example of colored inks that can be used for printing the translucent films is the Syntex Pantone Series, supplied by Kohl & Madden (Fort Lee, N.J.). The colored ink is then copied or printed onto each of a series of translucent films, using methods known to one skilled in the art. The films are commercially available and are made from various polymers. The translucent nature of the films allows them to simulate the translucent appearance of tooth enamel. An example of a film that may be used is Fasson® CRACK'N PEEL® 700 clear polyester, made by Avery Dennison Corporation (Graphics Division, Painesville, Ohio). These films may be self-adhering, partially self-adhering, non self-adhering, and combinations thereof, and have a thickness from about 1 mil to about 2 mil. To ensure the numerical assessment of color match, the color of the printed film may be quantitated, as previously described.

A dental professional can produce almost every different color found in human teeth using the method previously described. The method of making the inventive films is based upon custom shade tabs or chips to match different levels of color, or color mixes, that are found in human teeth by systematically diluting colors represented in existing porcelain systems and porcelain powders to different shades of colors. Almost a limitless number of shades of colors can be produced from any porcelain system using this approach.

The dimensions of color are described by Hegenbarth in *Creative Ceramic Color: A Practical System* (Quintessence Publishing Co., Inc 1989, Chicago) which is expressly incorporated by reference herein in its entirety. To understand color mixes they must be separated into their three principal properties: hue (color tone), value (color brightness), and chroma (color saturation). What are usually called "colors", such as red, green, blue, yellow, etc. are more precisely termed hues, although the more common term "color" is used in describing the inventive system. While hues may be intensified or diluted, they cannot be changed into other colors unless they are mixed with another hue.

The value, or brightness of a color, describes how much light of a particular color is reflected or absorbed by an object, or the point it takes on a gray scale between black and white. One way of understanding value is by the relationship between the object and its distance from a light source. If the object is nearer the light source, it appears brighter; if it is further away, it appears darker.

Chroma, or color saturation, describes the strength of purity of a particular hue. For transparent or translucent substances, such as enamel of teeth or baked dental porcelain powders, chroma depends on the thickness of the material. The thicker the substance, the more intense the effect of the color. This is also one source of the problems associated with the use of present shade guides to convey color: to achieve the color intensity of a conventional shade guide, the thickness of the porcelain layers must either be increased beyond clinical standards, or must be strengthened by the addition of intense color modifiers.

The inventive apparatus and method provide an array and form of reproducing these subtle colors of various porcelain systems, as well as their intensities and characterizations, in order to more closely approximate the colors of a human tooth, and to communicate these colors among dental professional and patients. Examples of such intensities and characterizations are found in Vanbini and Mangani, *Practical Procedures and Aesthetic Dentistry* (2001), 13, pp. 19–26, which is expressly incorporated by reference herein in its entirety. The inventive system provides a way to determine, and convey to a dental professional, the precise sequence and areas of films that will yield a dental prosthesis that most closely approximates the hue, chroma, and value, of the parts of the natural tooth or teeth that are being replaced.

In another embodiment, the invention provides a method to determine and communicate the patterns of opalescence on a tooth, which is due to the reflection of iridescent light by the tooth. The tooth enamel, due to its translucent character, is responsible for the opalescence of natural teeth. Enamel has the capacity to enhance the short wavelength component of the spectrum of light that it encounters, thus rendering life to the blue-gray shades that are evident at the incisal halo area of the tooth. Five common types of opalescence have been described by Vanbini and Mangani. In type 1, mamelon-like, the halo follows the incisal outline of the mamelon of the dentin body. Type 2, split mamelons, presents itself with a large mamelon divided by an accessory vertical groove. In type 3, comb-like, there are many small vertical grooves that create a "comb-like" halo. Type 4, window-like, presents itself as a regular halo that creates a narrow "window" between the dentin body and incisal margin. In type 5, stain-like, the halo is an amber stain that rises from the incisal margin towards the coronal/middle third in the shape of a triangle. These blue-gray shade patterns may be printed on translucent films, and sections of the film that contain the pattern may subsequently be placed on a template, or layered on another film, to match that found on the natural tooth.

In another embodiment, the common patterns of hypocalcification in human teeth, as also described by Vanbini and Mangani, can be conveyed by printing films with various white patterns that resemble hypocalcifications. Hypocalcified areas of the tooth are presented as dot like, and occasionally irregular, opaque, intense, milky white stains that are found in various areas of the tooth. The patterns in the enamel can appear as small, round white areas, small clouds, small white spots that are distributed in a uniform way, and/or white spots that are arranged in a horizontal band. A film, or a section of a film, that has the desired hypocalcifications pattern, may be placed on a template or layered on top of another film to obtain the desired effect.

In still another embodiment, the films include colors to indicate the value of a tooth, that is, its translucent grayness. One or more of these films are overlaid on the sequence of films that has matched the tooth color (more specifically, hue and chroma) to approximate the value. This advantageously eliminates the need for the dental professional to rely on costly plastic or porcelain facets to indicate value.

The series of translucent films, having one or more of the previously described representations of hue, chroma, value, opalescence, translucence, and hypocalcifications, may be configured in any shape. For example, the films may be shaped as squares, rectangles, triangles, or tooth-like structures. They may be cut into the shape of shade tabs or other models, or small sections.

To meet the need of approximating the complex shade patterns of human teeth, the films are layered or placed in a pattern or order that most closely approximates the desired color. This may be accomplished by placing the films on any sort of two dimensional or three-dimensional templates, such as a model tooth, a commercial color guide, or a colored photograph, until the colors match the tooth to the satisfaction of the dental professional and/or patient.

Figure 2:
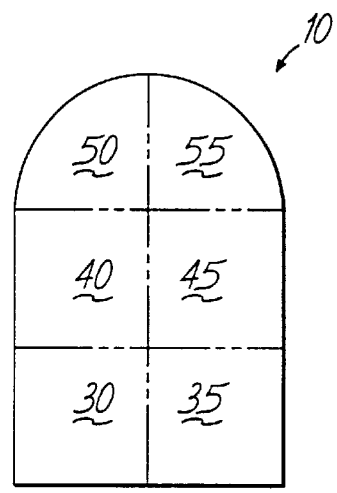
FIG. 2 illustrates six divisions of a tooth.

The films may or may not be divided into the shape of the section, or part, of the tooth to be matched. If divided, any number of divisions may be used. For example, as shown in FIG. 1, a film 10, which may be in a shape generally representing a tooth, may be divided into three parts: cervical 15, middle 20, and incisal 25 to represent parts of a tooth. In another example, as shown in FIG. 2, the films may also be further divided equally at the middle from cervical to incisal to make total six parts, three on a mesial surface 30, 40, and 50, and three on a distal surface 35, 45, and 55. The locations of the distal and mesial surfaces of the tooth that are represented in FIG. 2 may be reversed, depending upon the tooth's location in the jaw. The distal surface of the tooth is that which is farthest from the middle of the front jaw; the mesial surface is that which is closest to the middle of the front jaw. The films may also be cut into smaller sections and shapes, as desired by the dental professional. Alternatively, the films may have no divisions.

The divisions on the film corresponding to the different areas of the tooth are made as perforations, deep creases, markings, or any other indicators that allow the dental professional to easily remove a desired section from the rest of the film and place the section onto a template. The films themselves may also be of various sizes that can be further configured at the discretion of the dental professional to obtain the desired shade or shades of color of the particular tooth area or surface that is being matched.

Figure 3:
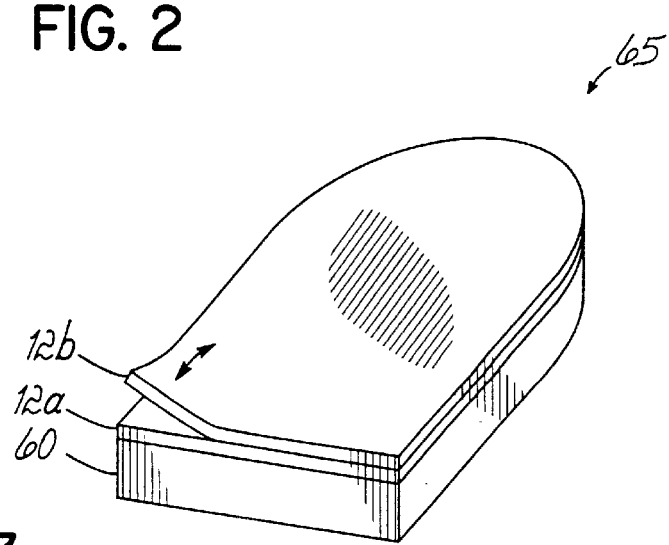
FIG. 3 illustrates the positioning of films on a template.

In another embodiment, the individual films are removably self-adhesive. As shown in FIG. 3, the film 12a can be pressed onto the appropriate area of a shade tab of one of the dental shade guide systems, or on another appropriate type of template 60, using a convenient means or technique, such as with fingers, forceps, or other appropriate devices. Once a section of film is placed on a template, a section of a film 12b of the same or a different color may be placed either partially or completely under or on top of it to more closely approximate the natural tooth color. To obtain an even more accurate match for the color of different areas of the dental prosthesis, the films may be configured into smaller pieces and/or shapes, and any number of films may be layered until the desired color is obtained on the final film/template assembly 65. A film, or section of film, may also be removed and replaced with another colored film.

In an additional embodiment, each film bears an indicium which identify or codes its matching composition and color in a custom or commercial shade guide system, such as a porcelain shade guide system. The indicium may be further described, either on the film itself, and/or in an index accompanying the film system. Such codes facilitate communication between various dental professionals and minimizes subjective interpretations. For example, a dental professional can send a technician a modified template containing the films, with the indexed sections of film corresponding to the tooth area(s) precisely defined, or just the desired codes for the films, with reference to the index. Alternatively, the dental professional can simply describe on a tooth diagram, which may be either a hard copy or via software, the index numbers of the films used on various sections of the template to obtain the desired colors. A dental technician can reproduce the same colors using his or her own template, if desired, and verify, clarify, or question the matching before beginning work, if necessary.

In other embodiments, the films, may be packaged, or formed, as multiple strips or sheets. These may be of any desired size, and may be organized, for example, in a reversibly bound or perforated booklet, a bundle, a wheel, a palette, or in any other type of format for ease in selection and use. Any other packaging or organizing system may also be employed. Dental professionals may also use the various sizes and shapes of the films to experiment with various colors. This allows visualization of the desired color or shade and facilitates comparisons to the resulting color of baked porcelain mixtures.

In yet another embodiment, the films may be used to match the colors of a tooth or teeth that are shown or printed on other types of films, photographs, computer generated models, digitized photographic models, and the like.

It should be understood that the embodiments of the present invention shown and described in the specification are only preferred embodiments of the inventor who is skilled in the art and are not limiting in any way. For example, the invention may be used in veterinary practice to convey tooth color of a nonhuman animal. For another example, the invention may be used in cosmetic dentistry to approximate a color other than that of a natural tooth, for example, for patients wishing to have a prosthesis that is "whiter" than their natural tooth, that lacks the hypocalcifications found in their natural tooth, etc. Therefore, various changes, modifications or alterations to these embodiments may be made or resorted to without departing from the spirit of the invention and the scope of the following claims.

What is claimed is:

1. A method to convey color distribution in at least one area of a tooth comprising providing a plurality of translucent films, each of said films in a color found in teeth and having an indicium for said color, capable of layering to achieve a color approximating that of said area, layering said films or sections of said films on a template in an order until said color is approximated, repeatedly layering said films or sections of said films on said template or on a film or a section of film until said color distribution for a plurality of areas of said tooth is approximated, and conveying said color distribution to a dental professional.

2. The method of claim 1 wherein said template is selected from the group consisting of dental shade guides, dental models, colored photographs, dentures, crown, bridges, and combinations thereof.

3. The method of claim 1 wherein said films approximate properties selected from the group consisting of chroma, hue, value, opalescence, hypocalcifications, and combinations thereof.

4. The method of claim 1 wherein said indicium is selected from the group consisting of bar codes, letters, numbers, and combinations thereof.

5. The method of claim 1 wherein layering comprises placing, removing, and replacing a plurality of said films on said template.

6. The method of claim 5 wherein said layering comprises configuring said films to a shape of said template.

7. The method of claim 5 wherein said layering comprises configuring said films to a size of said template.

8. The method of claim 1 wherein said films are selected from the group consisting of self-adhering films, partially self-adhering films, non-self-adhering films, and combinations thereof.

9. The method of claim 1 further comprising using said indicium to convey said color distribution.

* * * * *